US00PP36925P2

(12) United States Plant Patent
Mussche

(10) Patent No.: US PP36,925 P2
(45) Date of Patent: Sep. 2, 2025

(54) ***CISSUS* PLANT NAMED 'G4Y0001'**

(50) Latin Name: ***Cissus discolor* Blume.**
Varietal Denomination: G4Y0001

(71) Applicant: FLORALI LICENSING B.V., Rijswijk (NL)

(72) Inventor: Erik Mussche, Bogor (ID)

(73) Assignee: Floralí Licensing B.V., Rijswijk (NL)

( * ) Notice: Subject to any disclaimer, the term of this patent is extended or adjusted under 35 U.S.C. 154(b) by 0 days.

(21) Appl. No.: 19/207,175

(22) Filed: May 13, 2025

(51) Int. Cl.
*A01H 6/88* (2018.01)
*A01H 5/12* (2018.01)

(52) U.S. Cl.
USPC ..... Plt./226

(58) Field of Classification Search
USPC ..... Plt./226, 343
CPC ..... A01H 6/88; A01H 6/00; A01H 5/12
See application file for complete search history.

*Primary Examiner* — Keith O. Robinson
(74) *Attorney, Agent, or Firm* — James R. Holm; Plant Novelty Rights, LLC

(57) ABSTRACT

A new and distinct *Cissus* plant named 'G4Y0001' particularly distinguished by a climbing growth habit suitable for use as a trellised potted plant, yellow-green juvenile foliage with a silvery greyed-green hue over the whole upper leaf surface and an axillary band of greyed-purple in the center, and greyed-green mature foliage on the upper surface that fades to a lighter greyed-green in the center.

3 Drawing Sheets

Figure 1:
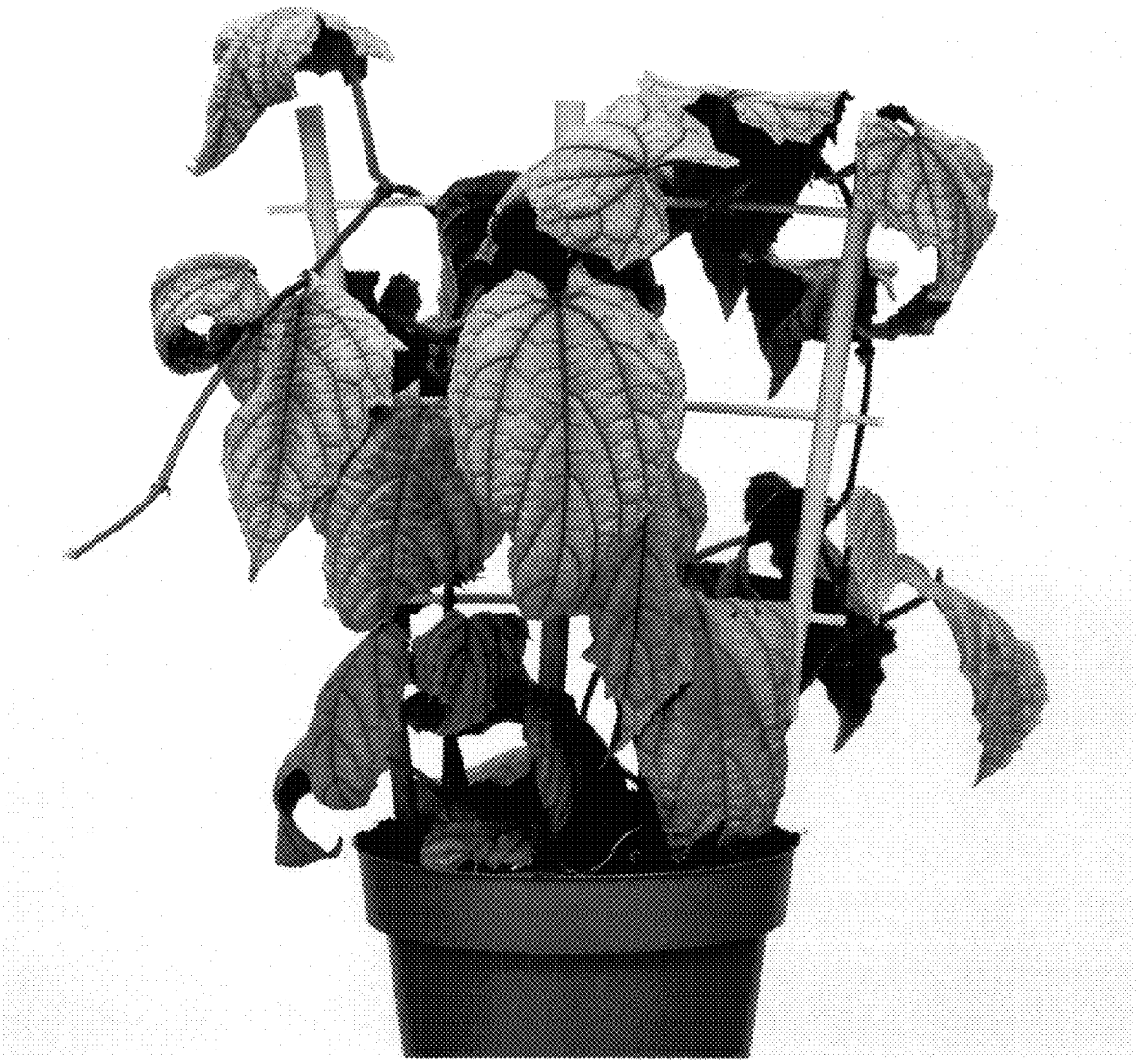

Genus and species: *Cissus discolor* Blume.
Variety denomination: 'G4Y0001'.

BACKGROUND OF THE NEW PLANT

The present invention comprises a new and distinct variety of *Cissus* plant, botanically known as *Cissus discolor*, and hereinafter referred to by the variety name 'G4Y0001'.

This new *Cissus* plant was discovered in July 2022 by the inventor as a naturally occurring whole plant mutation (sport) growing amongst the unnamed and unpatented cultivated species of *Cissus discolor* Blume plants in a greenhouse located in Bogor, Indonesia.

The new cultivar was selected based on its greyed-green leaf color and greyed-purple leaf venation. 'G4Y0001' was first reproduced asexually using vegetative meristem tip cuttings in Bogor, Indonesia in September 2022. Asexual propagation by vegetative meristem tip cuttings of the new variety has shown that the unique features of the new variety are stable and reproduced true-to-type to date through eleven successive generations.

Plant Breeder's Rights for this variety have been applied for under CPVO application No. 20/232,571 on Nov. 30, 2023. 'G4Y0001' has not been made publicly available or sold anywhere in the world more than one-year prior to the filing date of the present U.S. patent application.

SUMMARY OF THE INVENTION

The new *Cissus* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Cissus* variety. The combination of these characteristics distinguishes 'G4Y0001' as a new and distinct variety of *Cissus*.

1. 'G4Y0001' exhibits a climbing growth habit suitable for use as a trellised potted plant;
2. 'G4Y0001' exhibits yellow-green juvenile foliage with a silvery greyed-green hue over the whole upper leaf surface and an axillary band of greyed-purple in the center; and
3. 'G4Y0001' exhibits greyed-green mature foliage on the upper surface that fades to a lighter greyed-green in the center.

The new *Cissus* cultivar can be distinguished from its progenitor or parent species *Cissus discolor* by having mature leaves colored greyed-green with greyed-purple venation on the upper surface, whereas the progenitor or parent species *Cissus discolor* has mature leaves colored white with green venation on the upper surface.

The new *Cissus* cultivar can be distinguished from the related known variety of *Cissus rhombifolia* 'Mandaiana' (unpatented) in the following characteristics:

1. 'GY40001' has ovate shaped leaves, whereas 'Mandaiana' has distinctly tri-lobed, rhomboid shaped leaves that resemble grapevine foliage.
2. 'GY40001' has bicolored leaves with a light green base and greyed-purple central coloring along the midrib and leaf margins on the upper surface. In contrast, 'Mandaiana' has leaves that are uniformly dark green on the upper surface.
3. 'GY40001' has leaves that are greyed-purple on the lower surface, whereas the lower surface of leaves of Mandaiana are typically light green.
4. 'GY40001' has a leaf venation that is deeply sunken on the upper surface, contributing to its textured appearance. In contrast, 'Mandaiana' has smoother foliage with less prominent venation on the upper leaf surface.
5. 'GY40001' has greyed-purple petioles, whereas 'Mandaiana' has green petioles.

DESCRIPTION OF THE PHOTOGRAPHS

This new *Cissus* cultivar is illustrated by the accompanying-colored photographs which show the overall appearance and distinct characteristics of the plant. The colors shown are as true as can be reasonably obtained by conventional photographic procedures. The photographs are of a 3-month-old plant grown in a 14-centimeter circular container in a greenhouse in Naaldwijk, The Netherlands. Colors in the photographs may differ slightly from the color values cited in the botanical description which accurately describes the colors of the new variety.

FIG. 1. shows a side view of the overall plant form and foliage of 'G4Y0001'.

Figure 2:
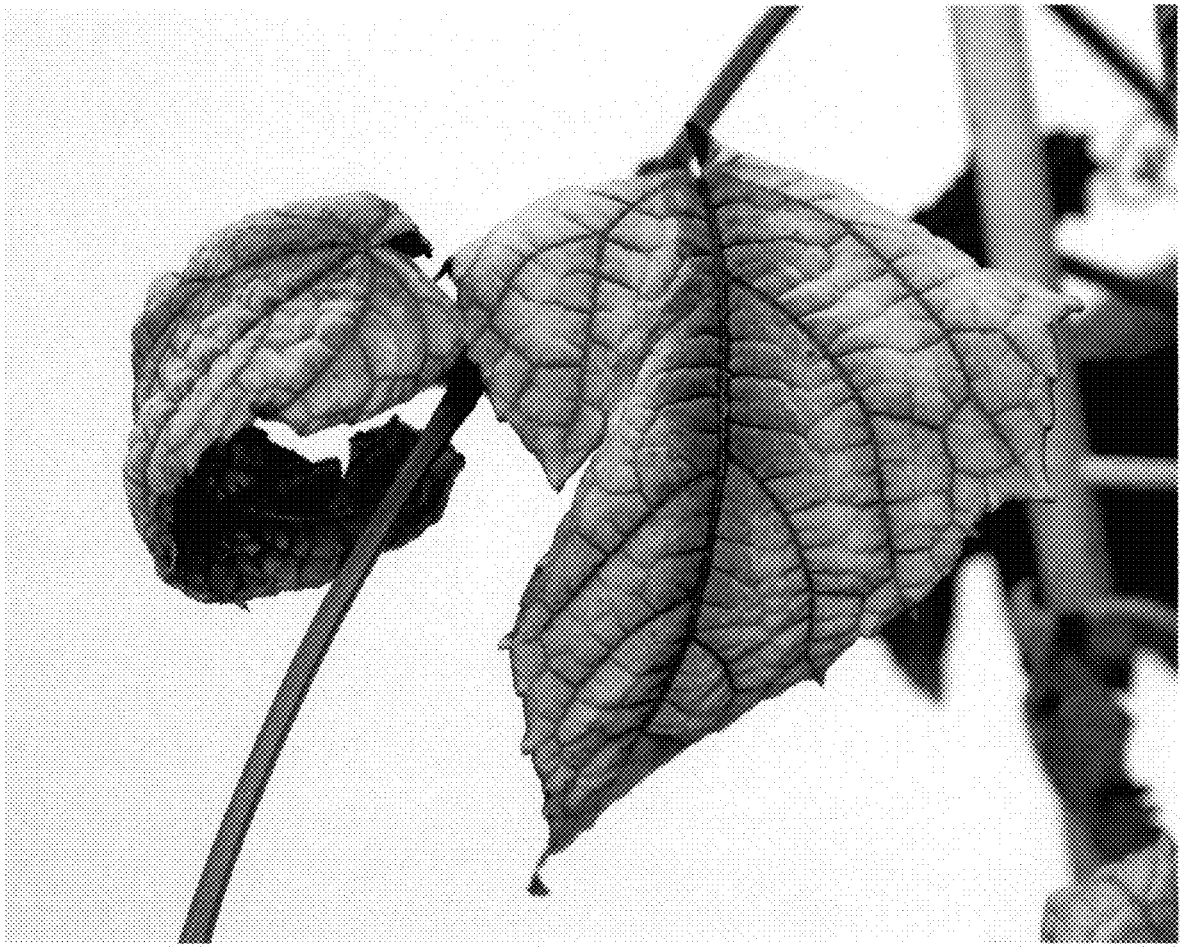

FIG. 2. shows a closeup of the upper surface of a juvenile leaf of 'G4Y0001'.

Figure 3:
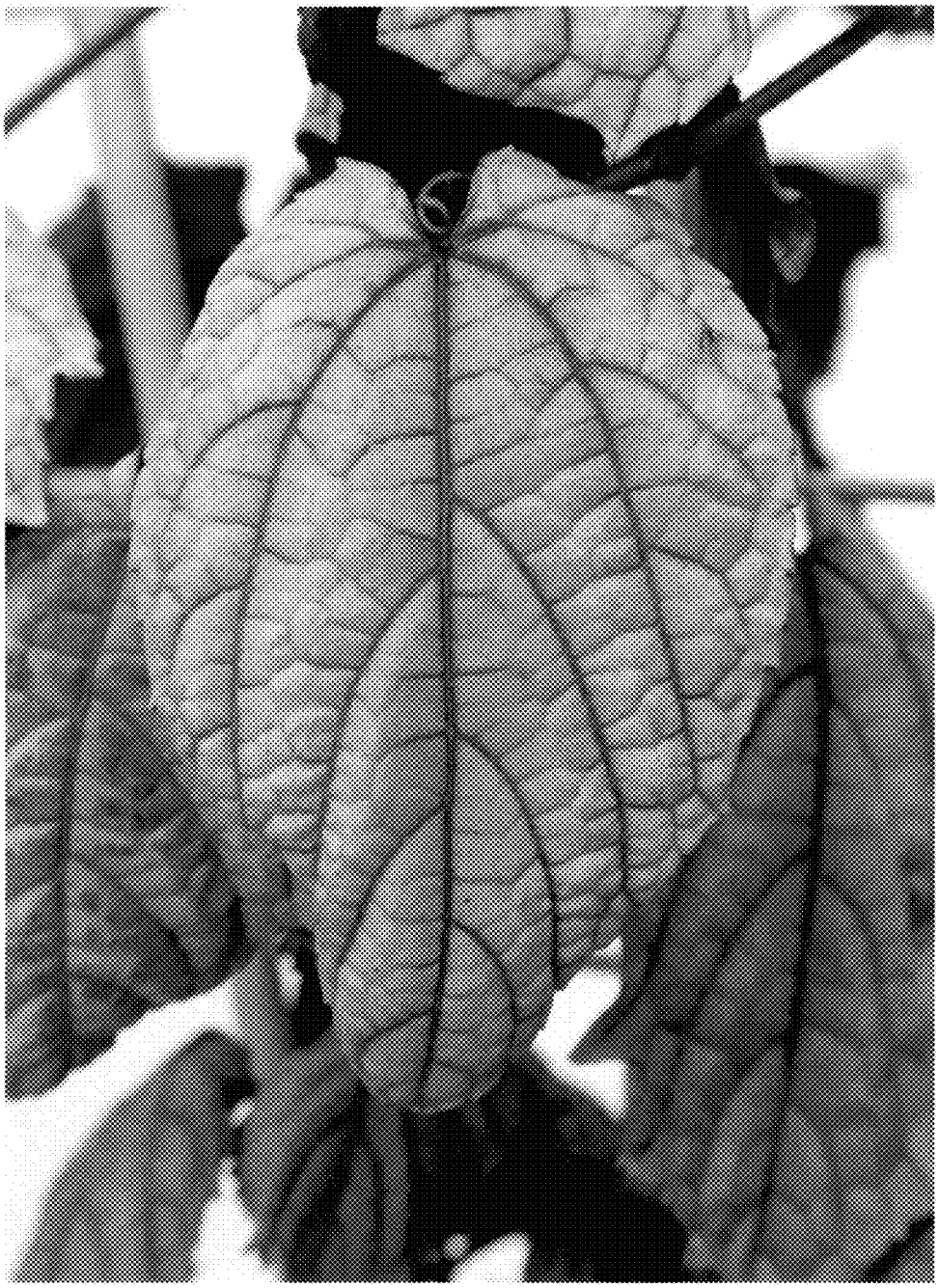

FIG. 3. shows a closeup of the upper surface of a mature leaf of 'G4Y0001'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a conventional greenhouse in Naaldwijk, The Netherlands. Plants were grown under 279-foot candles (3,000 lux) with a daily and nightly temperature range of 12 to 18 degrees Celsius. Detailed descriptions were taken in April 2024 from 3-month-old plants grown in 14-centimeter circular containers. Measurements and numerical values represent averages of typical plant types.

DETAILED BOTANICAL DESCRIPTION

Classification:

*Family*.—Vitaceae.

*Botanical*.—*Cissus discolor* Blume.

*Common*.—*Cissus*, Rex Begonia Vine.

*Denomination*.—'G4Y0001'.

General description:

*Plant type*.—Tropical perennial vine for use as a potted evergreen plant or shrub.

*Growth habit*.—Climbing, cultivated on trellises and canes.

*Overall plant shape*.—Narrow, ovate.

*Height from soil level to top of foliar plane*.—27.0 cm on a trellis measuring 23.0 cm in height.

*Plant spread*.—30.3 cm.

*Growth rate*.—Moderate.

*Plant vigor*.—Moderate to high.

*Branching habit*.—Basal shoots with few lateral branches.

*Propagation type*.—Vegetative meristem tip cuttings.

Branch description:

*Number of main branches per plant*.—Average 2.

*Number of lateral branches per plant*.—Average 2.

*Primary branch length*.—Average 49.9 cm.

*Primary branch diameter*.—Average 0.3 cm.

*Internode length of primary branches*.—Average 5.2 cm.

*Primary branch appearance and shape*.—Angled, 5 sided.

*Primary branch luster*.—Matte.

*Primary branch aspect/angle from horizontal*.—Average 55° at the base and varying between 20° and 90°.

*Primary branch strength*.—Flexible and strong.

*Primary branch color*.—Developing branches: Slightly darker than 197A (greyed-green). Mature branches: A blend of 148A and 197A (yellow-green to greyed-green). Internodes: A blend of near 148A and 197A (yellow-green to greyed-green).

*Primary branch surface characteristics*.—Moderately covered with small glands visible as pustulate dots with an average of 0.5 mm in diameter and 0.4 mm or less in height and colored near 162C (greyed-yellow).

Foliage description:

*Arrangement*.—Alternate.

*Division*.—Simple.

*Attachment*.—Petiolate.

*Quantity of foliage*.—Average of 10 leaves per primary branch.

*Lamina*.—Shape: Ovate. Length: 12.1 cm. Width: 6.9 cm. Aspect: Slightly convex and slightly to strongly curved. Apex shape: Apiculate to near apiculate. Base shape: Cordate. Texture: Upper surface: Slightly leathery, smooth and glabrous. Lower surface: Smooth, glabrous, and moderately covered with small glands which are visible as flattened pustulate dots; dots average 1.0 mm in diameter and 0.4 mm or less in height and colored near 161D (greyed-yellow). Rugosity (both upper and lower surfaces): Slight to moderate. Luster: Upper surface: Matte, moderately velvety on mature leaves, young leaves are very velvety. Lower surface: Matte. Margins: Entire, serrated and moderately undulate. Color: Juvenile foliage: Upper surface: Near 147B (yellow-green) with a N187A (greyed-purple) axillary band in the center and a silvery hue of close to 190A (greyed-green) over the whole leaf surface. Lower surface: Near N186C (greyed-purple) fading to slightly darker than 148A (yellow-green) towards the margins, base and apex. Mature foliage: Upper surface: A blend of N189B and N189C (greyed green) fading to slightly lighter than N189B in the center. Lower surface: Near N186C and 187A (greyed-purple) fading to near 197A (greyed-green) at the margin, base and apex. Venation: Pattern: Pinnate. Color (mature leaves): Upper surface: Near 183A (greyed-purple) fading to near 147B (yellow-green) towards the apex. Lower surface: Near 186C (greyed-purple).

*Petiole*.—Length: Average 4.8 cm. Diameter: Average 0.3 cm. Texture: Smooth, glabrous with 5 axial ribs. Luster: Slightly glossy. Strength: Medium. Color: Upper surface: Near N186C (greyed-purple) and slightly lighter. Lower surface: A blend of near 177A (greyed-orange) and 183B (greyed-purple).

*Stipules*.—Two leafy stipules present at the base of the petiole (one on each side); broad ovate to near triangular in shape; average of 0.4 cm in length and 0.3 cm in width; colored near 146C (greyed green) and fading to a translucent near 197D (greyed-green) towards the margins and apex.

*Tendrils*.—A single, heavily curled tendril present at each node opposite the petiole attachment; average of 9.0 cm in length and 0.1 cm in diameter; cleft on the upper 2.0 cm; colored near 178B (greyed-red).

Inflorescence: None observed to date.

Heat tolerance: Tolerant to temperatures up to 40 degrees Celsius.

Cold tolerance: At least hardy to USDA zone 11.

USDA hardiness zones: Zones 11 to 13.

Rain tolerance: Moderate.

Wind tolerance: Low to Moderate.

Disease and pest tolerance: No claims are made to any superior disease or insect tolerance with this cultivar. However, 'G4Y0001' has shown less susceptibility to spider mites (*Tetranychidae*), especially with adequate humidity. 'G4Y0001' has shown a lower incidence of mealybugs (*Pseudococcus* spp.) compared to other tropical foliage plants. 'G4Y0001' is less affected by whiteflies (*Aleyrodidae*) when grown under standard greenhouse conditions. 'G4Y0001' shows tolerance to powdery mildew (*Erysiphales*) when provided with good air circulation and dry foliage.

What is claimed is:

1. A new and distinct variety of *Cissus* plant named 'G4Y0001', substantially as illustrated and described herein.

* * * * *